(12) United States Patent
Kühn et al.

(10) Patent No.: US 6,548,079 B1
(45) Date of Patent: Apr. 15, 2003

(54) MOXIFLOXACIN FORMULATION CONTAINING COMMON SALT

(75) Inventors: Bernd Kühn, Köln (DE); Hans-Friedrich Mahler, Köln (DE); Michael Eisele, Bergisch Gladbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/049,095

(22) PCT Filed: Jul. 25, 2000

(86) PCT No.: PCT/EP00/07098

§ 371 (c)(1), (2), (4) Date: Feb. 5, 2002

(87) PCT Pub. No.: WO01/10465

PCT Pub. Date: Feb. 15, 2001

(30) Foreign Application Priority Data

Aug. 6, 1999  (DE) .......................... 199 37 116

(51) Int. Cl.[7] ................................................ A61F 2/02
(52) U.S. Cl. ...................................................... 424/423
(58) Field of Search ......................................... 424/423

(56) References Cited

U.S. PATENT DOCUMENTS

| | | | |
|---|---|---|---|
| 4,957,922 A | 9/1990 | Lammens et al. | 514/255 |
| 5,084,276 A | 1/1992 | Yunker et al. | 424/422 |
| 5,478,829 A | 12/1995 | Conrath et al. | 514/254 |
| 5,563,149 A | 10/1996 | Jung et al. | 514/300 |
| 5,677,316 A | * 10/1997 | Ao et al. | 514/312 |
| 5,811,130 A | 9/1998 | Boettner et al. | 424/643 |

FOREIGN PATENT DOCUMENTS

| | | |
|---|---|---|
| EP | 0219784 | 4/1987 |
| EP | 0534860 | 9/1992 |
| EP | 0507851 | 4/1997 |
| WO | 9109525 | 7/1991 |
| WO | 0018386 | 4/2000 |
| WO | 0110465 | 2/2001 |

* cited by examiner

*Primary Examiner*—Carlos Azpuru
(74) *Attorney, Agent, or Firm*—Jerrie L. Chiu

(57) ABSTRACT

The present invention relates to an aqueous formulation comprising moxifloxacin hydrochloride and sodium chloride, to the formulation for use as a medicament and to the use of the formulation for preparing a medicament for preventing or treating bacterial infections in humans or animals.

11 Claims, No Drawings

MOXIFLOXACIN FORMULATION CONTAINING COMMON SALT

This application is a 371 continuation of PCT/EP00/07098 filed Jul. 25, 2000.

FIELD OF THE INVENTION

The present invention relates to an aqueous formulation comprising moxifloxacin hydrochloride and sodium chloride, to the formulation for use as a medicament and to the use of the formulation for preparing a medicament for preventing or treating bacterial infections in humans or animals.

BACKGROUND

Moxifloxacin (INN—International Nonproprietary Name) is an antibiotic from the class of the quinolonecarboxylic acids of the following formula:

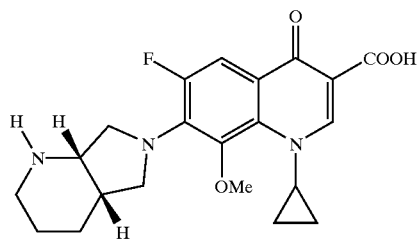

1-cyclopropyl-7-([S,S]-2,8-diazabicyclo[4.3.0]non-8-yl)-6-fluoro-1,4-dihydro-8-methoxy-4-oxo-3-quinolonecarboxylic acid It is a highly effective anti-infective agent and was described for the first time in EP-A-0 350 733. However, EP-A-0 350 733 does not describe any pharmaceutical preparations which are suitable for parenteral administration. Such solutions for infusion, which can be administered parenterally, are, however, needed for treating patients in intensive care units which cannot be treated orally.

For formulating solutions for infusion which are acceptable, it is necessary to adjust the osmolality to the physiological conditions of the organism (Sucker/Fuchs/Speiser; Pharmazeutische Technologie). Relatively pronounced hypo- or hyperosmotic variations can result in erythrocyte damage and/or tissue irritation. The i.v. administration of relatively strong hypoosmotic solutions leads to haemolysis, and administration of relatively large amounts of hyperosmotic solutions leads to plasmolysis. Hypoosmotic solutions contain fewer dissolved molecules or ions than are present in the blood or the tissue fluid. In this case, isotonization has to be carried out by addition of isotonizing agents (Bauer/Frömming/Führer, Pharmazeutische Technologie). A range from 270 to 350 mOsmol/kg is considered to be isotonically suitable.

Commercial isotonic solutions are, for example, a 5% strength glucose solution or a 0.9% strength sodium chloride solution.

EP-A-0534860 describes formulations of the quinolonecarboxylic acid antibiotic sparfloxacin with monocarboxyl-polyhydroxy acids or lactones thereof, such as, for example, ascorbic acid, and with glucose or glycerol as isotonizing additive. The invention is based on improving the solubility of sparfloxacin by means of monocarboxyl-polyhydroxy acids to obtain acceptable, isotonic or hypertonic formulations of suitable concentrations.

U.S. Pat. No. 5,563,149 describes the formulation of aqueous solutions of pyridonecarboxylic acids and esters and salts thereof as antibiotics as ready-to-use solutions for injection or infusion or concentrates for injection or infusion. Details about isotonization additives or about the tonicity of the formulations are not given. The object of said invention is to improve the solubility of the pyridonecarboxylic acids described.

EP-A-0507851 describes formulations comprising quinolonecarboxylic acid/metal ion acid complexes. It has been found that the solubility of the active compound is increased when polyvalent metal ions in the form of magnesium, calcium, manganese, zinc, cadmium, aluminium, cerium or iron ions are added, as a consequence of complex formation at neutral pH. Such formulations are described as being chemically and physically stable, even in the presence of glucose for isotonization, and are better tolerated, owing to a neutral pH.

U.S. Pat. No. 5,811,130 describes metal ion complexes with danofloxacin where in particular magnesium and zinc ions are used for complex formation and with which the solubility of danofloxacin is increased considerably. Formulations with high active compound concentration for subcutaneous injection are described which can only be achieved by the improved solubility of the metal ion/active compound complexes in water.

Furthermore, U.S. Pat. No. 5,084,276 teaches the use of quinolonecarboxylic acid/metal ion complexes, for example with magnesium, calcium, manganese, zinc, cadmium, iron-(II) and iron-(III) or cerium-(IV) ions for complexing the active compounds temafloxacin, toxyfloxacin or pefloxacin, where the active compound complexes are used together with excipients for reducing irritation of the veins. The formulations for parenteral infusion described are isotonized with glucose.

SUMMARY OF THE INVENTION

During the development work on moxifloxacin, it was surprisingly found that isotonization by addition of 5% commercial glucose or other sugars or sugar alcohols, such as 2.5% glycerol, gives unstable solutions in the case of moxifloxacin. This instability manifests itself by the occurrence of subvisual particles in the solution, the number of which exceeds the range permissible by the pharmacopoeias (USP XXIII, BP93). During storage, brown amorphous particles are formed, which frequently only occur after 4–8 weeks of storage at 40° C., and the number of which increases further during storage. At room temperature or on storage in the refrigerator, the formation of these particles is slower. We found that the particle formation is caused by a three-fold interaction between moxifloxacin and/or its salts, iron and sugar or sugar alcohols, such as glycerol. This was surprising, since similar phenomena in the formulation of parenteral formulations of quinolonecarboxylic acid have hitherto not been known, and in particular EP 0507851, U.S. Pat. No. 5,811,130 and U.S. Pat. No. 5,084,276 utilize the interaction of polyvalent metal ions with quinolonecarboxylic acids for stabilization and increasing solubility. The antibiotic ciprofloxacin, for example, tolerates considerably higher concentrations of iron.

Since the element iron is ubiquitous and is present in particular in the feedstock glucose, in which it may be bound in complex form, such a formulation can be prepared only at a great expense, both analytically and for quality assurance. In addition, the use of steel in the production plants is problematic, and only selected steels and controlled materials are allowed to come into contact with the solution. Furthermore, such a formulation requires, in principle, extremely iron-deficient active compound qualities which can only be prepared at great expense. In the case of moxifloxacin, solutions having an iron content above 20 ppb exhibit a particle content which increases considerably over time, so that, after the preparation, the required pharmaceutical quality of the formulations cannot be maintained for the stability period required. Moreover, glucose-isotonized formulations are considered to be very disadvantageous in various fields of clinical application, since they may represent additional stress for the energy balance of the patient and require special attention, in particular in the treatment of diabetics.

For parenteral aqueous formulations of hydrochlorides of quinolonecarboxylic acids there is, owing to their poor solubility properties in the presence of NaCl, the general problem of administering the composition with an acceptable infusion volume. In addition to the above-described possibility of increasing the solubility by metal complex formation, various possibilities of salt formation have also been explored.

Thus, EP-A-0219784 describes solutions for infusion of ciprofloxacin with physiologically acceptable acids. Also described is a formulation of 75 mg of ciprofloxacin/500 ml (0.015% w/v), 0.203 ml of 1 M hydrochloric acid/500 ml (corresponding to a molar ratio of ciprofloxacin/hydrochloric acid of 1.0 to 0.9) and 4.5 g of sodium chloride/500 ml (0.9%) as isotonization additive. This active compound concentration corresponds approximately to the saturation solubility of the active compound in the stated formulation at room temperature. Higher concentrations of ciprofloxacin in the presence of hydrochloric acid and isotonic amounts of NaCl cannot be realized, owing to the poor solubility of ciprofloxacin and its hydrochloride. At a customary dosage of ciprofloxacin of 100 to 400 mg per dose, 2 to 3 times per day, this results in unacceptable infusion volumes of about 1.31 to 81 per day. Because the amount of infusion liquid at a stated dosage would be very high, preference is therefore given to using aqueous formulations of ciprofloxacin-lactate, which is better soluble.

Initially, we have found, surprisingly, that drug formulations of moxifloxacin hydrochloride which are isotonized with sodium chloride are not sensitive to iron ions. However, the solubility properties of the active compound moxifloxacin in the form of its hydrochloride in the presence of sodium chloride are extremely poor, so that initial attempts to develop such formulations were, after precipitations had occurred, given up for the time being. Surprisingly, however, it was found that it is possible to prepare acceptable formulations of moxifloxacin hydrochloride using isotonization with sodium chloride if certain narrow concentration ranges for active compound and isotonizing agent are adhered to.

DETAILED DESCRIPTION OF THE INVENTION

Accordingly, the invention provides aqueous formulations comprising from 0.04% to 0.4% of moxifloxacin hydrochloride (based on the moxifloxacin) and from 0.4% to 0.9% (w/v) of sodium chloride.

An aqueous formulation means that the components of the formulation are present in water.

The expression "% (w/v)" means weight in g per 100 ml of volume, i.e. g/100 ml.

The aqueous formulation of the invention preferably comprises from 0.08% to 0.32% (w/v) of moxifloxacin HCl (based on the moxifloxacin) and particularly preferably from 0.1% (w/v) to 0.2% (w/v) of moxifloxacin HCl (based on the moxifloxacin). Very particular preference is given to a formulation comprising about 0.16% (w/v) of moxifloxacin HCl (based on the moxifloxacin), corresponding to 400 mg/250 ml.

The aqueous formulation according to the invention comprises from 0.4% to 0.9% (w/v) of sodium chloride, preferably from 0.5% to 0.9% (w/v) of sodium chloride, particularly preferably from 0.7% to 0.9% (w/v) of sodium chloride, and very particular preference is given to an amount of sodium chloride of approximately 0.8% (w/v).

For a dosage range of from 100 mg to 1000 mg at active compound concentrations of from 0.04% to 0.4% (w/v) of moxifloxacin hydrochloride, it is thus possible to adjust the osmotic pressure to physiological conditions by adding from 0.4% to 0.9% of sodium chloride. To this end, it is necessary to take into account the saturation solubility of the active compound in the presence of the different sodium chloride concentrations at a temperature of 5° C. and to establish an optimum ratio according to the invention of active compound concentration and sodium chloride concentration. The saturation solubility of the active compound in the presence of the amounts of sodium chloride required for isotonization, measured at 5° C., must not be exceeded. This ensures that, even on short-term cold storage, there is no precipitation of the active compound as a result of exceeding the saturation solubilities.

For solutions of an active compound concentration of more than about 0.2% (w/v) of moxifloxacin HCl, it is not possible to prepare optimally isotonized solutions using sodium chloride, since the solubility of the substance becomes too low. Since, in the case of intravenously administered solutions, however, the solution for infusion is rapidly and painlessly diluted by the blood, it is sufficient to adjust the tonicity to the physiological conditions in the best possible manner. By adjusting the rate of infusion appropriately, it is possible to make sure that these solutions are tolerated optimally (Lit. Sucker/Fuchs/Speiser, "Pharmazeutische Technologie", Thieme Verlag 1991, p. 460 ff.).

An isotonic solution is a solution which has an osmotic pressure of about 270 to 330 mOsmol. This corresponds to a sodium chloride solution of a concentration of about 0.8% to 0.9% (w/v). In contrast, moxifloxacin HCl makes hardly any contribution to isotonization. It has surprisingly been found that, in the presence of this NaCl concentration, moxifloxacin HCl dissolves in sufficient quantity and in stable form, so that such a formulation is suitable for use as a formulation for parenteral administration.

TABLE 1

Solubility of moxifloxacin HCl in the presence of sodium chloride at 5° C.

| NaCl % (w/v) | 0 | 0.1 | 0.2 | 0.3 | 0.4 | 0.5 | 0.6 | 0.7 | 0.8 | 0.9 |
|---|---|---|---|---|---|---|---|---|---|---|
| Solubility moxifloxacin HCl % (w/v) | 1.8 | 1.1 | 0.7 | 0.5 | 0.4 | 0.3 | 0.2 | 0.2 | 0.2 | 0.1 |

Particular preference is given to a dosage of from 200 mg to 800 mg of moxifloxacin, corresponding to concentrations of from 0.08% to 0.32% (w/v) of moxifloxacin. The osmotic pressure is adjusted using 0.9% to 0.4% (w/v) of sodium chloride. Very particular preference is given to a dosage of 400 mg of moxifloxacin in the form of an approximately 0.16% strength (w/v) solution of moxifloxacin. This is isotonized using about 0.8% (w/v) of sodium chloride.

Furthermore, it has been found that the preparation of such solutions of moxifloxacin with sodium chloride requires considerable time if the active compound moxifloxacin hydrochloride is to be introduced and dissolved in a customary manner in an initial charge of the sodium chloride dissolved in water. This requires a stirring time of several hours to achieve a clear solution of the formulation and to avoid subsequent loss of the active compound by separating off the active compound in filtration steps. Using a process where the active compound is first dissolved in water and the sodium chloride is added only afterwards, it is possible to prepare the solution within a few minutes, allowing a more efficient production on an industrial scale.

The invention accordingly also provides a process for preparing the aqueous formulation according to the invention, in which a solution of the moxifloxacin hydrochloride in water is prepared initially, and sodium chloride is then added and dissolved.

The aqueous formulation of moxifloxacin hydrochloride is advantageously prepared by diluting a solution of moxifloxacin hydrochloride in water having a moxifloxacin hydrochloride concentration (based on the amount of moxifloxacin) of more than 0.4% (w/v) to 2.4% (w/v), i.e. a moxifloxacin hydrochloride concentrate in water, with an aqueous solution which comprises sodium chloride, to the moxifloxacin hydrochloride concentration according to the invention.

Thus, the invention also provides the use of an aqueous solution of moxifloxacin hydrochloride in water having a moxifloxacin hydrochloride concentration (based on the amount of moxifloxacin) of more than 0.4% (w/v) to 2.4% (w/v) (hereinbelow occasionally referred to as active compound concentrate) for preparing a medicament for parenteral administration, and a combination preparation comprising, separated from one another, an aqueous solution of moxifloxacin hydrochloride in water having a moxifloxacin hydrochloride concentration (based on the amount of moxifloxacin) of from more than 0.4% (w/v) to 2.4% (w/v) and an aqueous solution comprising sodium chloride, where the concentrated aqueous solution of the moxifloxacin hydrochloride is advantageously mixed by the treating physician or the nurse with the enclosed aqueous solution comprising sodium chloride.

The concentrated aqueous solution of moxifloxacin hydrochloride contains from 0.4% (w/v) to 2.4% (w/v) of moxifloxacin hydrochloride (based on the amount of moxifloxacin). The maximum concentration of the aqueous solution is limited by the saturation solubility of approximately 2.4% (w/v). The active compound concentrate preferably contains from 1.0 to 2.0% (w/v) of moxifloxacin hydrochloride (based on the amount of moxifloxacin), particularly preferably 2.0% (w/v) of moxifloxacin hydrochloride (based on the amount of moxifloxacin). The active compound concentrate is filled into suitable containers and sterilized in an appropriate manner. The containers can be made both of glass and of plastic. The container material may comprise substances protecting the content in a particular manner, for example protection against light or protection against oxygen.

By mixing with sodium-chloride-containing solutions, the active compound concentrate is diluted to moxifloxacin use concentrations in accordance with the aqueous formulation according to the invention. If appropriate, the solutions for diluting the active compound concentrate may, in addition to sodium chloride, also contain other salts with sodium, potassium, calcium, magnesium and the like, such as chlorides, carbonates, sulphates, acetates, gluconates, lactates, malates, and other auxiliaries and the like which are customary in the field of parenteral administration forms, as long as formation of a homogeneous solution for infusion is ensured. For diluting the active compound concentrate, it is also possible to employ customary, commercially available infusion carrier solutions.

The aqueous formulation according to the invention serves advantageously as a medicament for parenteral administration, in particular as a medicament for preventing or treating bacterial infections. Parenteral administration includes, for example, intravenous, intra-arterial, subcutaneous, intramuscular and intraperitoneal administration, intravenous administration being the most important. A dose which is considered to be suitable is 400 mg of active compound, based on the betaine form, for intravenous infusion once per day. The daily infusion volume administered should not exceed 200 to 250 ml. At an amount of active compound of 400 mg, this results in an active compound concentration of about 0.16% (w/v), corresponding to 400 mg/250 ml.

The aqueous medicament formulation according to the invention may, in addition to the ingredients used according to the invention, comprise other auxiliaries which are customary in the field of parenteral administration forms, such as, for example, acids and bases for adjusting the pH, and customary preservatives and antioxidants.

It is extremely surprising that the formulations according to the invention of moxifloxacin are reconverted by simple warming to room temperature into clear, particle-free solutions, even after storage at low temperatures for several weeks, resulting in precipitation of the active compound. A ripening of the precipitation, i.e. formation of stable coarse crystal structures, was not observed, so that the formulation according to the present invention can be considered to be stable and safe for marketing.

Furthermore, for the production plants, it is sufficient to employ steel qualities of general pharmaceutical quality. This is because the formulations according to the invention are surprisingly, in contrast to formulations of moxifloxacin comprising sugar or sugar alcohols, stable in the presence of iron. The experiments described below involving the intentional addition of iron ions to the solution show that there is no particle formation in the solution, even at amounts of 1 ppm of iron, i.e. 50 times the amount of the limit which is permissible for a glucose formulation. Accordingly, the formulations according to the invention are, owing to their stability and the fact that they can be prepared in a simple manner, highly suitable for use as formulations for parenteral administration.

With a view to the examples below, the invention is illustrated in more detail.

EXAMPLES

Comparative Example 1

Isotonic moxifloxacin formulation, 0.2% (w/v) (400 mg/200 ml), isotonized with glucose 5%

| | |
|---|---|
| Moxifloxacin HCl | 0.2% (w/v)* |
| Glucose monohydrate | 5.0% (w/v) |
| Water for injection | 94.8% (w/v) |

*Amount based on moxifloxacin in the betaine form

The water is initially charged in a reaction vessel made of stainless steel of pharmaceutical quality, and the moxifloxacin hydrochloride is dissolved therein with stirring. The glucose (commercial quality, about 380 ppm of Fe) is added to the solution of the active compound and dissolved therein. The mixture is filtered through a 0.2 μm sterile filter and then filled, in portions of 200 ml, into infusion bottles, which are closed and sterilized at 121° C. in an autoclave for 20 min. The finished solution contains about 25 ppb of iron.

After storage at 40° C., the product which has been prepared has the following particle content values:

| | Particles ≧ 25 μm/ml (limit max. 2/ml; USP XXIII) | | |
|---|---|---|---|
| Storage conditions | Lot A | Lot B | Lot C |
| Initial examination | 0.6/ml | 0.6/ml | 0.7/ml |
| 4 weeks at 40° C. | 5.6/ml | 4.2/ml | 4.3/ml |

The product is not stable and shows, after only 4 weeks of storage at 40° C., an impermissible increase of the particle values, which does not meet the requirements of the pharmacopoeias.

Comparative Example 2

Moxifloxacin formulation 0.4% (w/v) (400 mg/100 ml), tonicity adjustment using sodium chloride 0.3%

| Moxifloxacin HCl | 0.4% (w/v)* |
|---|---|
| Sodium chloride | 0.3% (w/v) |
| Water for injection | 99.3% (w/v) |

*Amount based on moxifloxacin in the betaine form

The water is initially charged in a reaction vessel made of stainless steel, and moxifloxacin hydrochloride is dissolved therein with stirring. Sodium chloride is added to the solution of the active compound and dissolved therein. The mixture is filtered through a 0.2 μm sterile filter and in each case 100 ml are filled into infusion bottles which are closed and heated in an autoclave at 121° C. for 20 min.

The solution has an osmolality of about 100 mOsmol/kg and is accordingly hypotonic, which, at the customary rate at which parenteral solutions are administered, leads to haemolysis and painful administration.

Example 1

Moxifloxacin Formulation 0.16% (w/v) (400 mg/250 ml)

| Moxifloxacin HCl | 0.16% (w/v)* |
|---|---|
| Sodium chloride | 0.8% (w/v) |
| Water for injection | 99.04% (w/v) |

*Amount based on moxifloxacin in the betaine form

The water is initially charged in a reaction vessel made of glass, and moxifloxacin hydrochloride is dissolved therein with stirring. Sodium chloride is added to the solution of the active compound and dissolved therein. An Fe(III) chloride solution is added to the mixture. The mixture is filtered through a 0.2 μm sterile filter and in each case 250 ml are filled into an infusion bottle which is closed and heated in an autoclave at 121° C. for 20 min.

The particle status of the product which has been prepared has, after storage at room temperature and at 40° C., the following values:

Iron Content of the Solution 540 ppb

| Storage conditions | Particles ≧ 25 μm/ml (limit max. 2/ml; USP XXIII) |
|---|---|
| Initial examination | 0.00 |
| 4 weeks at 40° C. | 0.13 |
| 8 weeks at 40° C. | 0.17 |
| 8 weeks at 25° C. | 0.00 |

The solution was found to be storage-stable and not sensitive to iron ions.

Iron Content of the Solution <10 ppb

| Storage conditions | Particles ≧ 25 μm/ml (limit max. 2/ml; USP XXIII) |
|---|---|
| Initial examination | 0.07 |
| 12 weeks at 40° C. | 0.19 |
| 78 weeks at 25° C. | 0.07 |
| 78 weeks at 30° C. | 0.15 |

The solution was found to be storage-stable and not sensitive to iron ions.

Example 2

Moxifloxacin Formulation 0.1% (w/v) (100 mg/100 ml)

| Moxifloxacin HCl | 0.1% (w/v)* |
|---|---|
| Sodium chloride | 0.9% (w/v) |
| Water for injection | 99.0% (w/v) |

Osmolality: 313 mOsmol/kg
*Amount based on moxifloxacin in the betaine form

The water is initially charged in a reaction vessel made of stainless steel of pharmaceutical quality, and moxifloxacin hydrochloride is dissolved therein with stirring. Sodium chloride is added to the solution of the active compound and dissolved therein. The mixture is filtered through a 0.2 μm sterile filter and in each case 100 ml is filled into an infusion bottle which is closed and heated in an autoclave at 121° C. for 20 min.

The particle content of the product which has been prepared has, after storage at room temperature and at 40° C., the following values:

| Storage conditions | Particles ≧ 25 μm/ml (limit max. 2/ml; USP XXIII) |
|---|---|
| Initial examination | 0.03 |
| 4 weeks at 40° C. | 0.05 |
| 95 weeks at 25° C. | 0.16 |
| 156 weeks at 25° C. | 0.43 |

The solution was found to be storage-stable and insensitive to the preparation in containers made of steel of pharmaceutical quality in normal production units.

Example 3

Moxifloxacin Formulation 0.04% (w/v) (40 mg/100 ml)

| | |
|---|---|
| Moxifloxacin HCl | 0.04% (w/v)* |
| Sodium chloride | 0.9% (w/v) |
| Water for injection | ad 100 ml |

Osmolality: 310 mOsmol/kg
*Amount based on moxifloxacin in the betaine form

Example 4

Moxifloxacin Formulation 0.08% (w/v) (80 mg/100 ml)

| | |
|---|---|
| Moxifloxacin HCl | 0.08% (w/v)* |
| Sodium chloride | 0.9% (w/v) |
| Water for injection | ad 100 ml |

Osmolality: 312 mOsmol/kg
*Amount based on moxifloxacin in the betaine form

Example 5

Moxifloxacin Formulation 0.2% (w/v) (200 mg/100 ml)

| | |
|---|---|
| Moxifloxacin HCl | 0.2% (w/v)* |
| Sodium chloride | 0.8% (w/v) |
| Water for injection | ad 100 ml |

Osmolality: 283 mOsmol/kg
*Amount based on moxifloxacin in the betaine form

Example 6

Moxifloxacin Formulation 0.3% (w/v) (300 mg/100 ml)

| | |
|---|---|
| Moxifloxacin HCl | 0.3% (w/v)* |
| Sodium chloride | 0.5% (w/v) |
| Water for injection | ad 100 ml |

Osmolality: 186 mOsmol/kg
*Amount based on moxifloxacin in the betaine form

Example 7

Moxifloxacin Formulation 0.4% (w/v) (400 mg/100 ml)

| | |
|---|---|
| Moxifloxacin HCl | 0.4% (w/v)* |
| Sodium chloride | 0.4% (w/v) |
| Water for injection | ad 100 ml |

Osmolality: 155 mOsmol/kg
*Amount based on moxifloxacin in the betaine form

Example 8

Infusion Concentrate 2% (w/v) (400 mg/20 ml)

| | |
|---|---|
| Moxifloxacin hydrochloride | 400 mg (calculated as betaine) |
| Water for injection | ad 20 ml |

The water is initially charged in a mixing vessel made of stainless steel of pharmaceutical quality, and the moxifloxacin hydrochloride is dissolved therein with stirring. The solution is filtered through a 0.2 µm filter and in each case 20 ml are filled into an injection bottle made of glass which is closed and sterilized.

For use, the content of the injection bottle (400 mg of moxifloxacin in 20 ml) is removed using a syringe and, under aseptic conditions, added to and mixed with 230 ml of a commercial 0.9% sodium chloride solution. This gives an isotonic solution for infusion of the concentration 400 mg/250 ml, corresponding to 0.16% (w/v). The osmolality is 315 mOsmol/kg.

What is claimed is:

1. Aqueous formulation, comprising from 0.04% to 0.4% (w/v) (based on the amount of moxifloxacin) of moxifloxacin hydrochloride and from 0.4% to 0.9% (w/v) of sodium chloride.

2. Aqueous formulation according to claim 1, comprising from 0.08% to 0.32% (w/v) (based on the amount of moxifloxacin) of moxifloxacin hydrochloride.

3. Aqueous formulation according to claim 1, comprising from 0.1% (w/v) to 0.2% (w/v) (based on the amount of moxifloxacin) of moxifloxacin hydrochloride.

4. Aqueous formulation according to claim 1, comprising from 0.5% to 0.9% (w/v) of sodium chloride.

5. Aqueous formulation according to claim 1, comprising from 0.7% to 0.9% (w/v) of sodium chloride.

6. Process for preparing the aqueous formulation of moxifloxacin hydrochloride, in which a solution of the moxifloxacin hydrochloride in water is prepared initially, and sodium chloride is then added and dissolved.

7. Process for preparing the aqueous formulation of moxifloxacin hydrochloride according to claim 1, characterized in that a solution of moxifloxacin hydrochloride in water having a moxifloxacin hydrochloride concentration (based on the amount of moxifloxacin) of from more than 0.4% (w/v) to 2.4% (w/v) is mixed with an aqueous solution comprising sodium chloride.

8. A method of treating or preventing a disease comprising administering to a host in need thereof an effective amount of an aqueous solution of moxifloxacin hydrochloride in water having a moxifloxacin hydrochloride concentration (based on the amount of moxifloxacin) of from more than 0.4% (w/v) to 2.4% (w/v).

9. A combination preparation comprising an aqueous solution of moxifloxacin hydrochloride in water having a moxifloxacin hydrochloride concentration (based on the amount of moxifloxacin) of from more than 0.4% (w/v) to 2.4% (w/v) and an aqueous solution comprising sodium chloride, wherein said solutions are separated from one another.

10. A pharmaceutical composition comprising an aqueous formulation according to any of claims 1 to 5.

11. A method of preventing or treating bacterial infections in humans or animals comprising administering to a host in need thereof an effective amount of a formulation according to any of claims 1 to 5.

* * * * *